United States Patent
Wang

(10) Patent No.: US 7,771,989 B2
(45) Date of Patent: Aug. 10, 2010

(54) MICROMACHINED DIAGNOSTIC DEVICE WITH CONTROLLED FLOW OF FLUID AND REACTION

(75) Inventor: Yunlong Wang, Fremont, CA (US)

(73) Assignee: Micro Point Bioscience, Inc., Santa Clara, CA (US)

( * ) Notice: Subject to any disclaimer, the term of this patent is extended or adjusted under 35 U.S.C. 154(b) by 0 days.

(21) Appl. No.: 12/583,669

(22) Filed: Aug. 24, 2009

(65) Prior Publication Data

US 2010/0029014 A1    Feb. 4, 2010

Related U.S. Application Data

(62) Division of application No. 11/694,945, filed on Mar. 31, 2007, now Pat. No. 7,598,091.

(60) Provisional application No. 60/744,219, filed on Apr. 4, 2006.

(51) Int. Cl.
    *C12M 1/34*      (2006.01)
(52) U.S. Cl. .................................. 435/287.9
(58) Field of Classification Search ...... None
See application file for complete search history.

(56) References Cited

U.S. PATENT DOCUMENTS

| | | | |
|---|---|---|---|
| 5,017,342 A | 5/1991 | Haberzettl et al. | |
| 5,821,958 A | 10/1998 | Lim | |
| 6,027,202 A | 2/2000 | Narushima | |
| 6,130,098 A | 10/2000 | Handique et al. | |
| 6,143,248 A | 11/2000 | Kellogg et al. | |
| 6,561,224 B1 | 5/2003 | Cho | |
| 6,572,745 B2 | 6/2003 | Rappin et al. | |
| 6,596,239 B2 | 7/2003 | Williams et al. | |
| 6,887,362 B2 | 5/2005 | Huang et al. | |
| 6,905,882 B2 | 6/2005 | Buechler | |
| 6,911,132 B2 | 6/2005 | Pamula et al. | |
| 7,016,560 B2 | 3/2006 | Ticknor et al. | |
| 7,117,807 B2 | 10/2006 | Bohn, Jr. et al. | |
| 7,278,718 B2 | 10/2007 | Aruga et al. | |
| 2004/0171092 A1 | 9/2004 | Harris et al. | |
| 2007/0111303 A1* | 5/2007 | Inoue et al. | 435/287.2 |

\* cited by examiner

*Primary Examiner*—Ann Y Lam
(74) *Attorney, Agent, or Firm*—Quine Intellectual Property Law Group

(57) ABSTRACT

This invention relates to a micromachined microfluidics diagnostic device that comprises one or multiple assaying channels each of which is comprised a sample port, a first valve, a reaction chamber, a second valve, a fluid ejector array, a third valve, a buffer chamber, a capture zone and a waste chamber. Each of these device components are interconnected through microfluidic channels. This invention further relates to the method of operating a micromachined microfluidic diagnostic device. The flow of fluid in the microchannels is regulated through micromachined valves. The reaction of sample analytes with fluorescent tags and detection antibodies in the reaction chamber are enhanced by the micromachined active mixer. By ejecting reaction mixture onto the capture zone through micromachined fluid ejector array, the fluorescent tagged analytes bind with capturing antiodies on capture zone. The fluid ejector array further ejects buffer fluid to wash away unbound fluorescent tags.

9 Claims, 11 Drawing Sheets

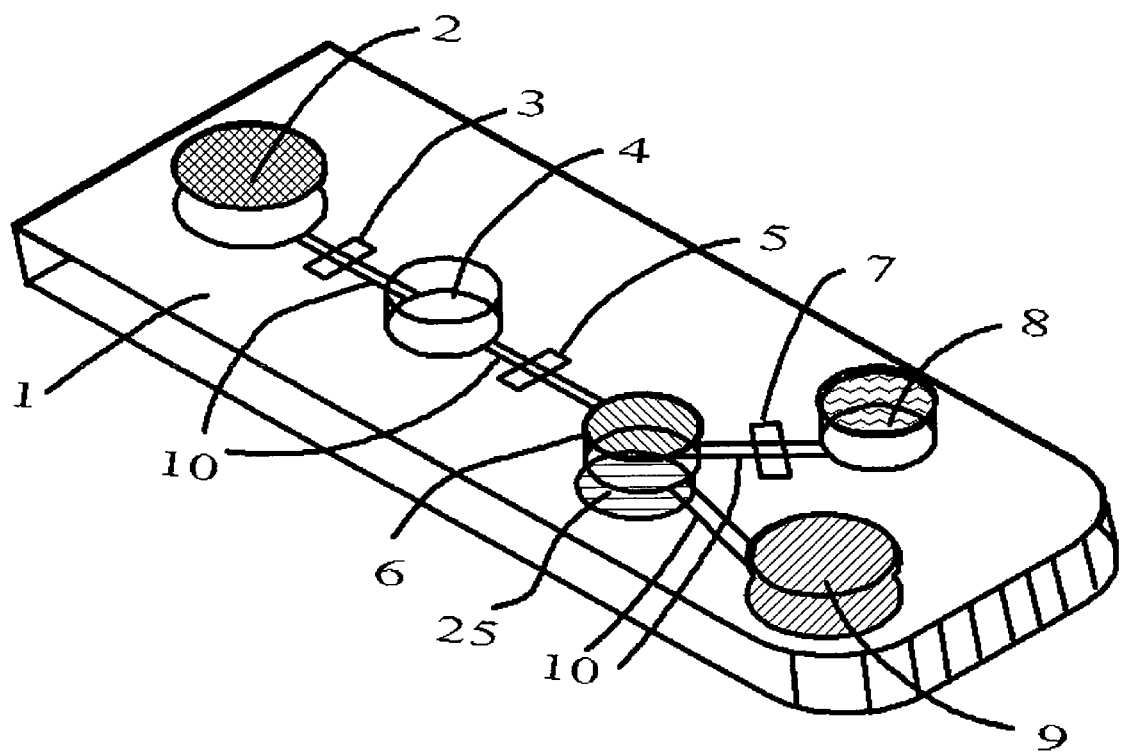
FIG_1

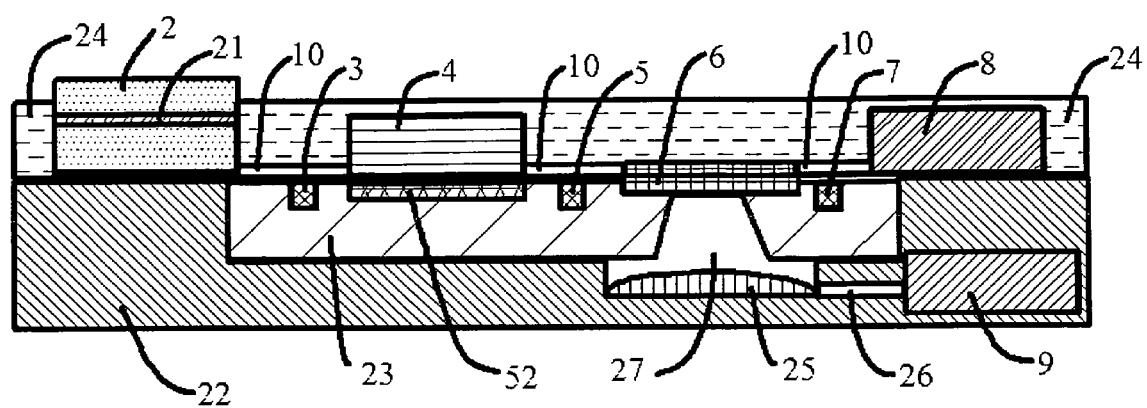
FIG_2

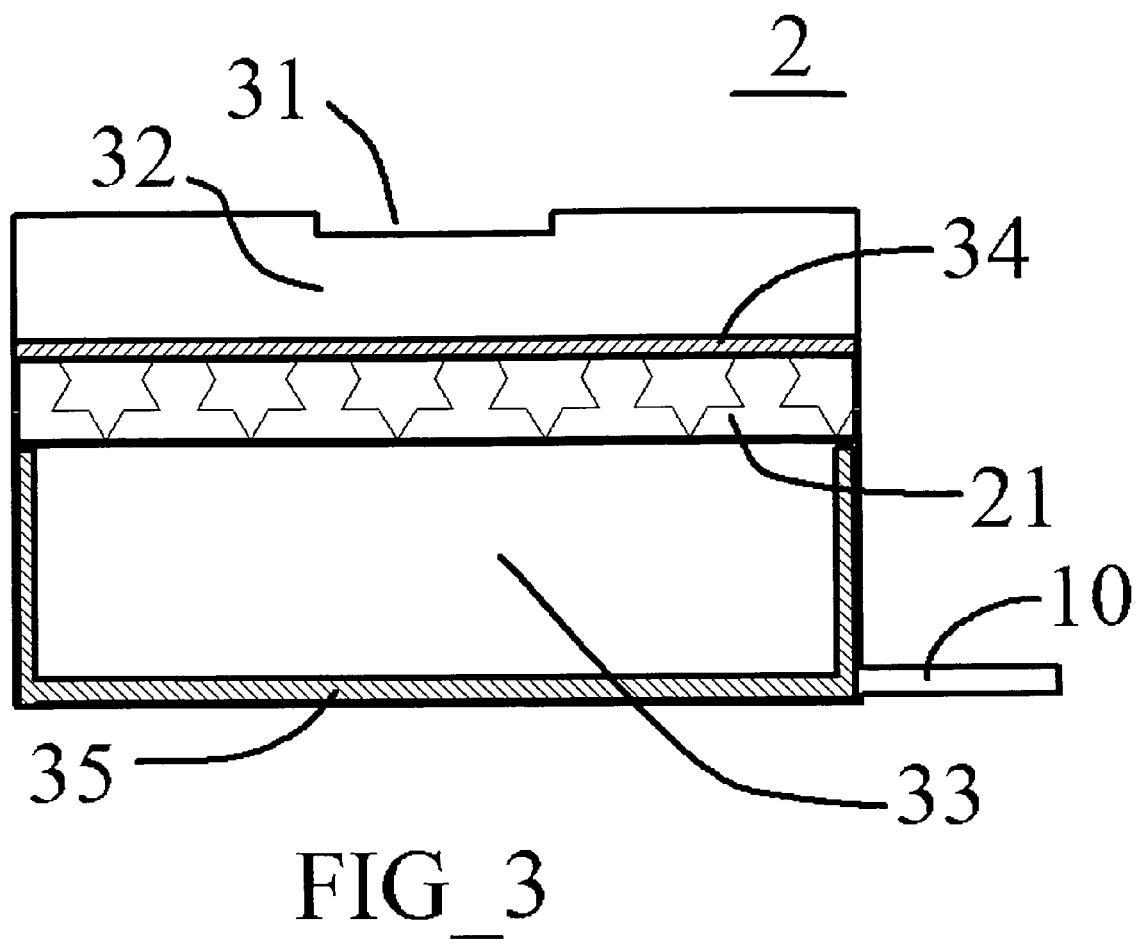
FIG_3

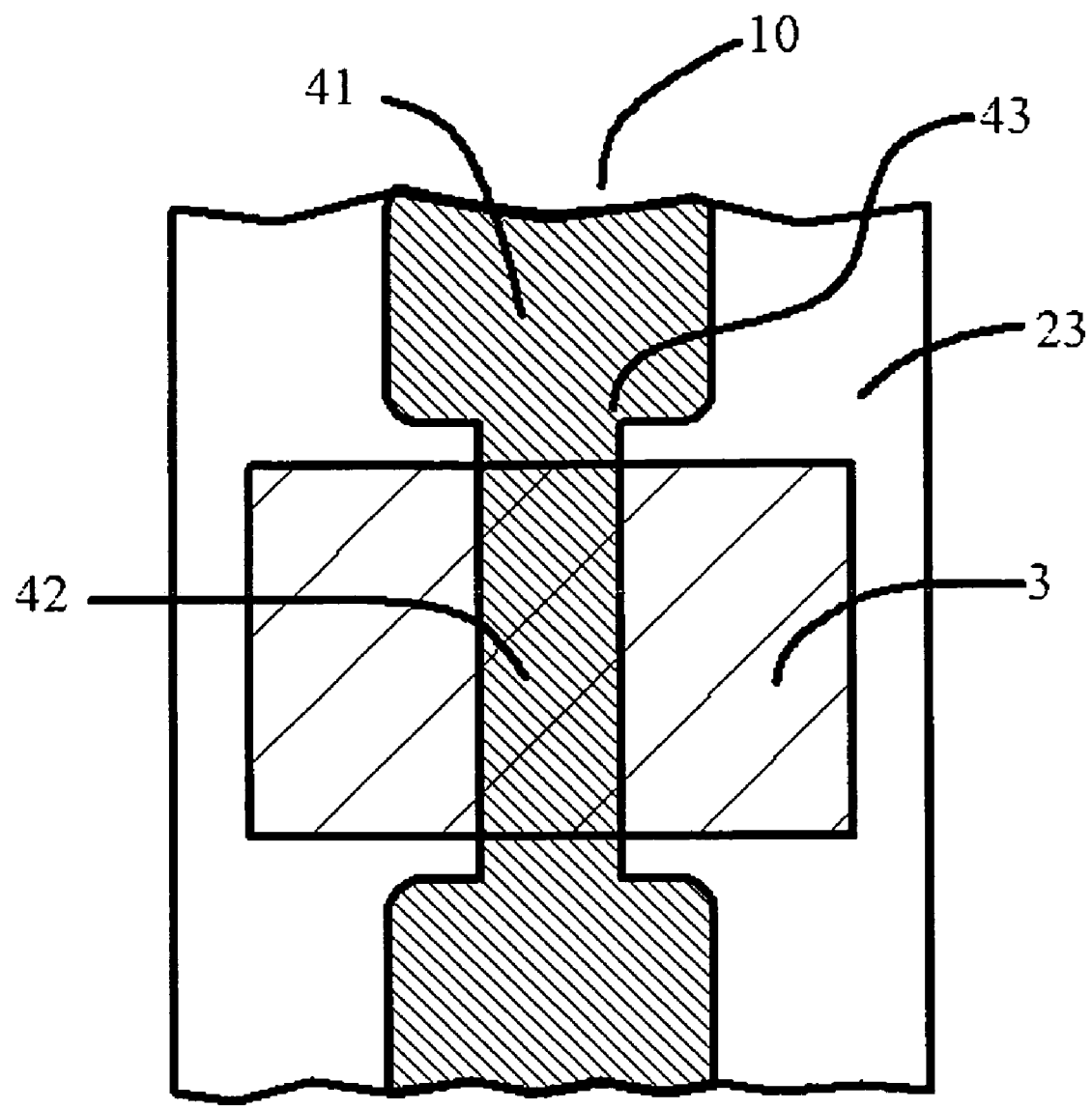
FIG_4

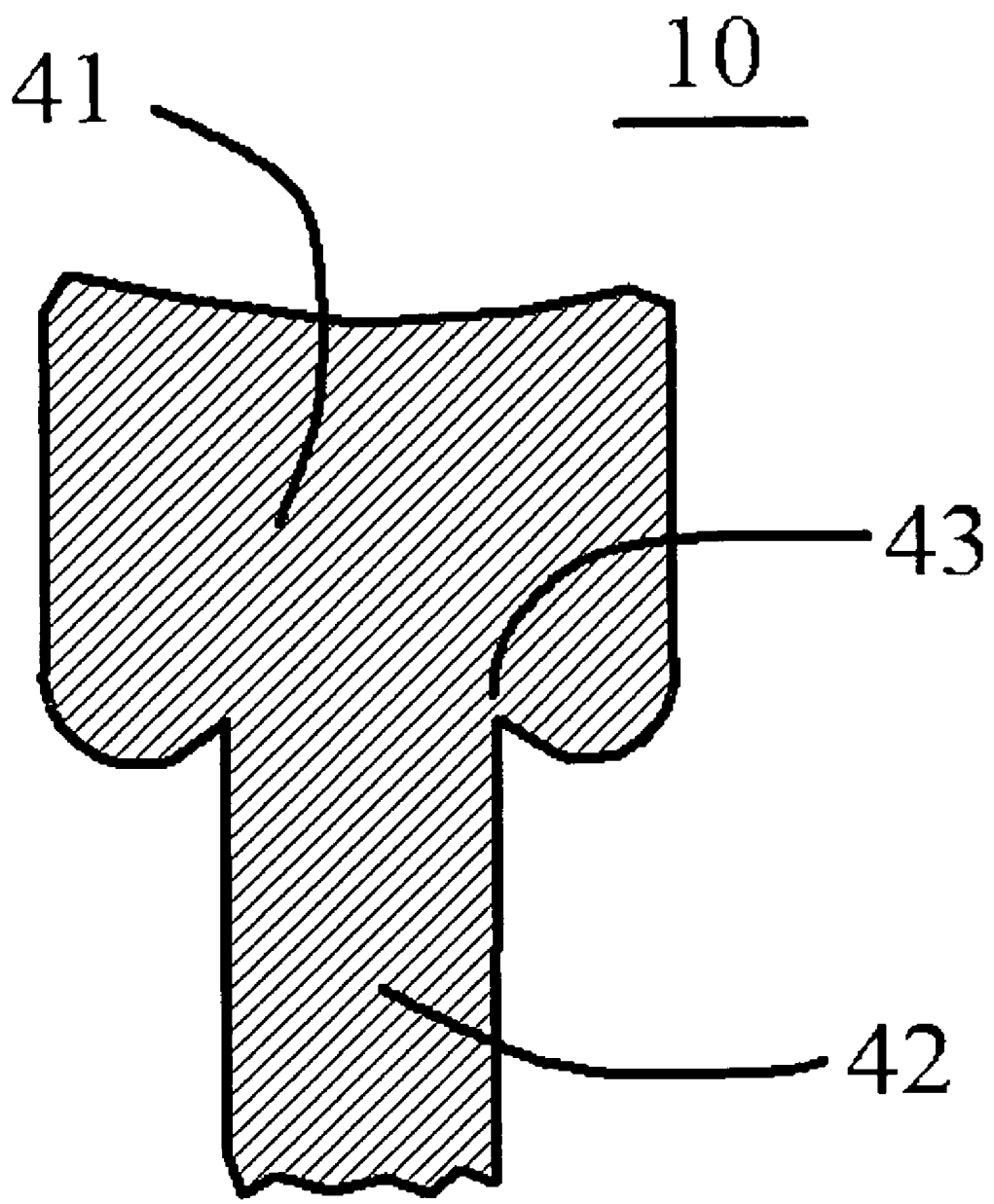
FIG_5

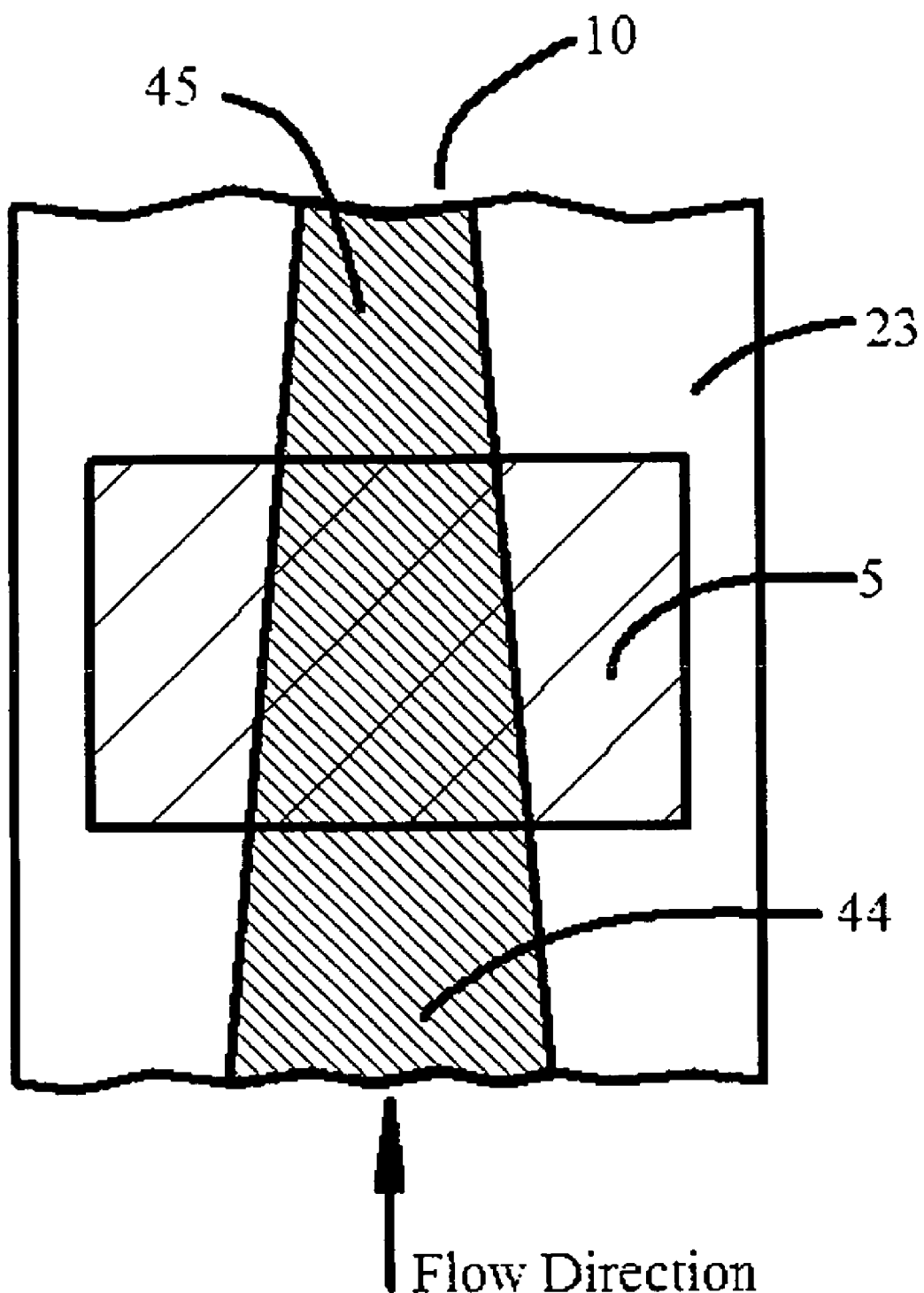
FIG_6

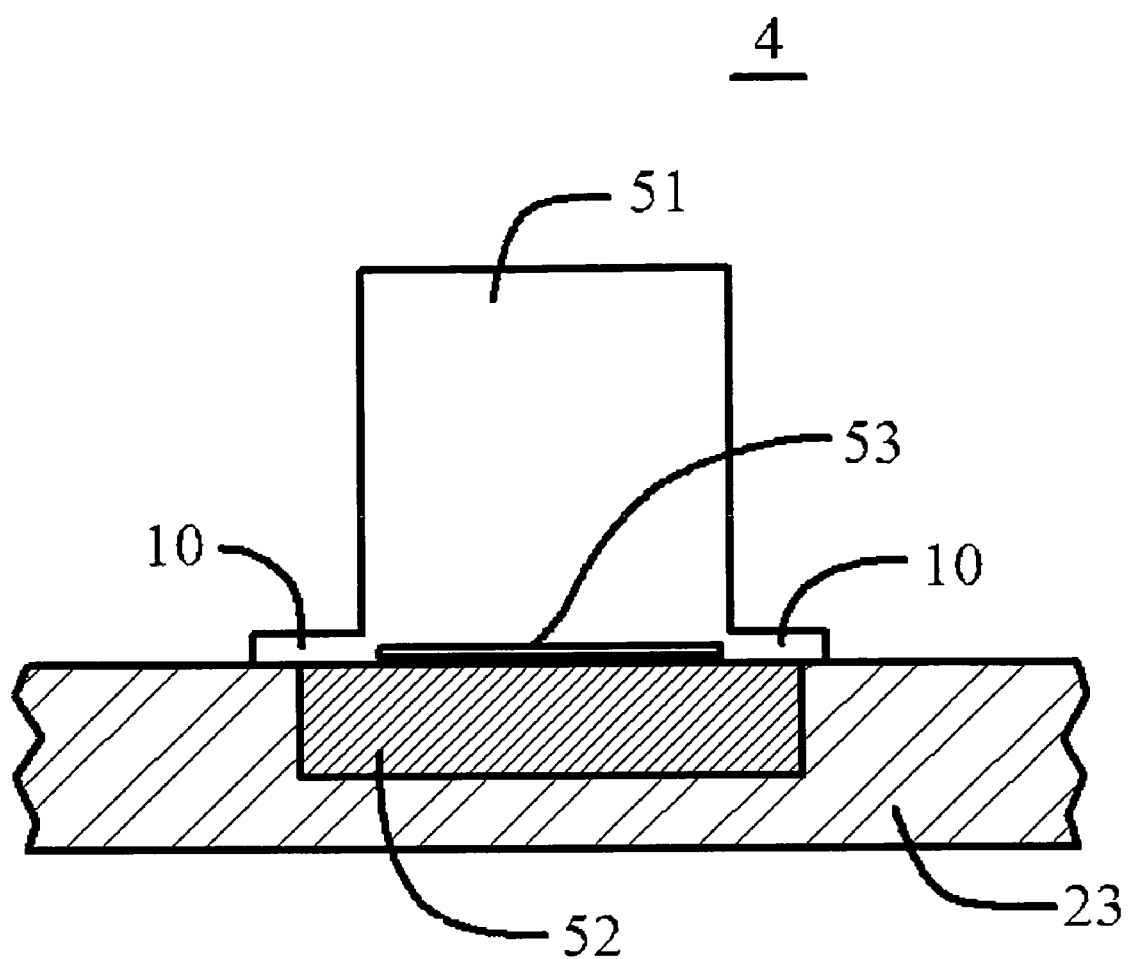
FIG_7

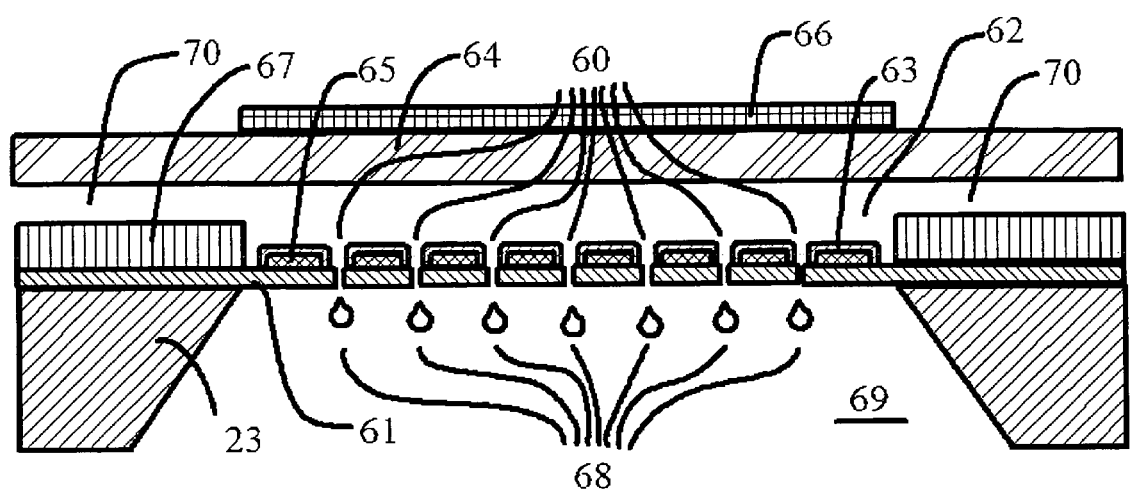
FIG_8

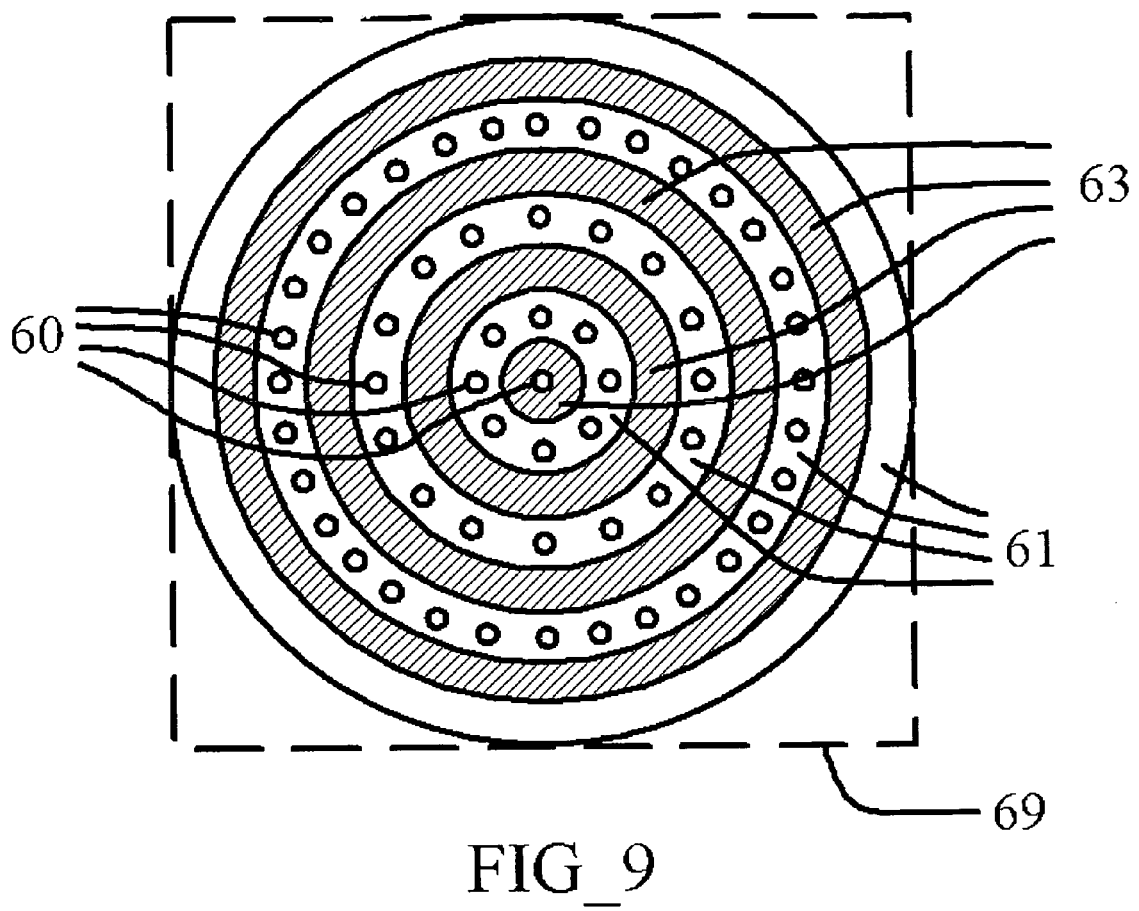
FIG_9

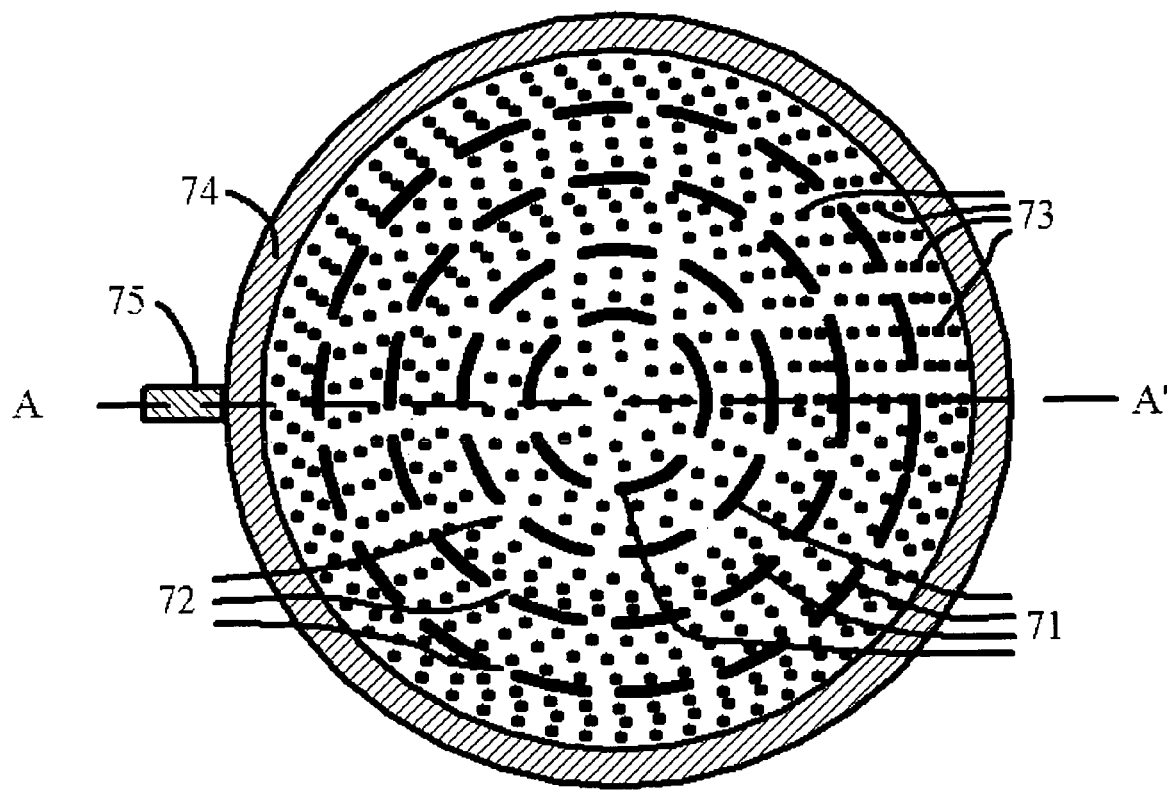
FIG_10

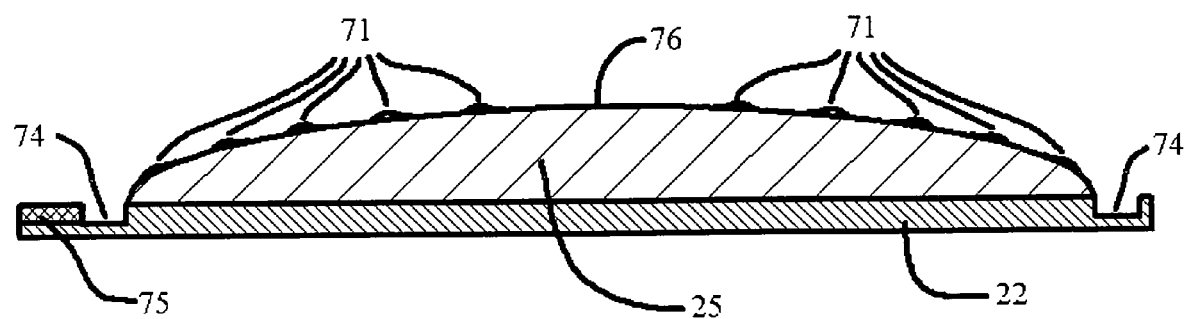
FIG_11

MICROMACHINED DIAGNOSTIC DEVICE WITH CONTROLLED FLOW OF FLUID AND REACTION

CROSS REFERENCE TO RELATED APPLICATION

This application is a divisional application from U.S. patent application Ser. No. 11/694,945, Micromachined Diagnostic Device with Controlled Flow of Fluid and Reaction, filed Mar. 31, 2007, now U.S. Pat. No. 7,598,091 which claims priority to and benefit of a prior U.S. Provisional Application No. 60/744,219, Micromachined Diagnostic Device with Controlled Flow of Fluid and Reaction, by Yunlong Wang, filed Apr. 4, 2006. The full disclosure of the prior application is incorporated herein by reference.

BACKGROUND OF THE INVENTION

Quantitative analysis of cells and analytes in fluid samples, particularly bodily fluid samples, often provides critical diagnostic and treatment information for physicians and patients. Quantitative immunoassays utilize the specificity of the antigen (Ag)-antibody (Ab) reaction to detect and quantitate the amount of an Ag or Ab in a sample. In solid phase immunoassays, one reagent (e.g., the Ag or Ab) is immobilized to a solid surface, facilitating separation of bound reagents or analytes from free reagents or analytes. The solid phase is exposed to a sample containing the analyte, which binds to its Ag or Ab; the extent of this binding is quantitated to provide a measure of the analyte concentration in the sample. Transduction of the binding event into a measurable signal, however, is affected by a number of interferences, such as variability in binding of components of the assay, which are not associated with the presence or amount of the analyte. These interferences limit the specificity and applicability of quantitative immunoassays.

Over the years, numerous simplified test systems have been designed to rapidly detect the presence of a target analytes of interest in biological, environmental and industrial fluids. In one of their simplest forms, these assay systems and devices usually involve the combination of a test reagent which is capable of reacting with the target analytes to give a visual response and an absorbent paper or membrane through which the test reagents flow. Paper products, glass fibers any nylon are commonly used for the absorbant materials of the devices. In certain cases, the portion of the absorbent member containing the test reagents is brought into contact, either physically or through capillarity, with the sample containing the target analytes. The contact may be accomplished in a variety of ways. Most commonly, an aqueous sample is allowed to traverse a porous or absorbent member, such as porous polyethylene or polypropylene or membranes by capillarity through the portion of the porous or absorbent member containing the test reagents. In other cases, the test reagents are pre-mixed outside the test device and then added to the absorbent member of the device to ultimately generate a signal.

With the advancement of microfluidics, it is possible that these diagnostic devices are made in a compact form to facilitate the immunoassays testing. In U.S. Pat. No. 6,905,882, it is reported the assay devices, assay systems and device components comprise at least two opposing surfaces disposed a capillary distance apart, at least one of which is capable of immobilizing at least one target analyte or a conjugate in an amount related to the presence or amount of target analyte in the sample from a fluid sample in a zone for controlled fluid movement to, through or away the zone. The device components may be incorporated into conventional assay devices with membranes or may be used in the inventive membraneless devices herein described and claimed. These components include flow control elements, measurement elements, time gates, elements for the elimination of pipetting steps, and generally, elements for the controlled flow, timing, delivery, incubation, separation, washing and other steps of the assay process.

Methods for quantitatively measuring the amount of an analyte of interest in a fluid sample are disclosed in U.S. Pub. No. 2004/0171092. The methods involve providing a membrane having an application point, a contact region comprising analyte-binding particles, a sample capture zone, and a control capture zone, where the contact region is between the application point and the sample capture zone, and the sample capture region is between the contact region and the control capture zone. In the assays, a fluid allows transport components of the assay by capillary action through the contact region, to and through the sample capture zone and subsequently to and through the control capture zone. In a "sandwich assay" embodiment, the amount of analyte in the fluid sample is related to a corrected analyte-binding particle amount, which can be determined, for example, as a ratio of the amount of analyte-binding particles in the sample capture zone and the amount of analyte-binding particles in the control capture zone. In a "competitive assay" embodiment, the membrane has an application point, a contact region comprising analyte-coated particles, a sample capture zone, and a control capture zone, where the contact region is between the application point and the sample capture zone, and the sample capture zone is between the contact region and the control capture zone. In this "competitive assay" embodiment, the amount of analyte in the fluid sample is inversely related to a corrected analyte-coated particle amount, which can be determined, for example, as a ratio of the amount of analyte-coated particles in the sample capture zone and the amount of analyte-coated particles in the control capture zone.

Active devices for immunoassays are also reported in U.S. Pat. No. 6,887,362. The report involves devices and methods for performing active, multi-step molecular and biological sample preparation and diagnostic analyses employing immunochemical techniques. It relates generally to bioparticle separation, bioparticle enrichment, and electric field-mediated immunochemical detection on active electronic matrix devices utilizing AC and DC electric fields. More specifically, the invention relates to devices and methods for sample preparation/manipulation, immunoimmobilization, and immunoassays, all of which can be conducted on one or more active electronic chip devices within a single system. These manipulations are useful in a variety of applications, including, for example, detection of pathogenic bacteria and biological warfare agents, point-of-care diagnostics, food or medical product quality control assays, and other biological assays.

Traditional immunoassay methods utilizing microtiterplate formats, dipsticks, etc., are labor and time extensive. Multiple steps requiring human intervention either during the process or between processes are sub-optimal in that there is a possibility of contamination and operator error. Further, the use of multiple machines or complicated robotic systems for performing the individual processes is often prohibitive except for the largest laboratories, both in terms of the expense and physical space requirements.

The microfluidics based devices reported in U.S. Pat. No. 6,905,882 and U.S. Pub. No. 2004/0171092 eliminated most parts of human intervention. However, the key parameters in the immunoassays process, such as the incubation time, the flow of fluid, and the mixing of fluorescent tags with detection antibody are accomplished with the passive capillary forces. The passive approach of moving fluid in microfluidics relies on the capillary force. Because each type of fluid has its own viscosity, and the fluid viscosity is also temperature dependant, the amount of fluid that flows in the microfluidics is hence not accurately controlled in these passive devices. The active device reported in the U.S. Pat. No. 6,887,362 relies on the electric field to move and analyze the analytes. This approach suffers from the limitation that analytes will have to be charged particles to be analyzed in the said devices.

OBJECTS AND SUMMARY OF THE INVENTION

It is an object of the present invention to provide a micromachined microfluidics diagnostic device.

It is another object of the present invention to provide a micromachined microfluidics diagnostic device and method for the controlled movement of fluids.

It is a further object of the present invention to provide a micromachined microfluidics diagnostic device that precisely controls the reaction between analytes, detection antibody, fluorescence tags and capturing antibody.

It is a further object of the present invention to provide a micromachined microfluidics diagnostic device that consumes a minimum quantity of patient blood sample.

It is another object of the present invention to provide a micromachined microfluidics diagnostic device that the reaction of analytes, detection antibody and fluorescence tags are aided by an active device to control the incubation time.

It is a further object of the present invention to provide a micromachined microfluidics device that the capture rate is henced by actively control the flow of reaction mixture onto the capture zone. The binding rate thus is increased.

It is another object of the present invention to provide a micromachined microfluidics diagnostic device that the washing of unbounded fluorescent tags in the capture zone is accomplished by controlling the active device to eject the washing buffer onto capture zone.

It is a further object of the present invention to provide a micromachined microfluidics diagnostic device that has a domed capture zone to increase the binding rate, and thus having better detection sensitivity.

The foregoing and other objects of the invention are achieved by a micromachined microfluidics diagnostic device that comprises a sample port, a first valve, a reaction chamber, a second valve, a fluid ejector array, a third valve, a buffer chamber, a capture zone and a waste chamber. Each of these device components are interconnected through microfluidic channels.

When the sample to be analyzed is added to the sample port, the first valve will initially stop the sample from flowing into the reaction chamber. After the first valve is applied with electric voltage or is actuated, the sample will then start flowing into the reaction chamber. The amount of sample fluid flowing into the reaction chamber is controlled by the time slapped between the opening and closing of the first valve, or by the reaction chamber volume in which case the reaction chamber is fully filled with sample fluid. The reaction chamber initially has dry coated fluorescent tags and detection antibodies, and may also have dry reagents.

During the filling process of sample fluid into the reaction chamber, the second valve is closed. When the determined amount of sample fluid is filled into the reaction chamber, the first valve is then closed. The active mixer embedded at in the reaction chamber is actuated to aid the mixing of analytes in the sample fluid with fluorescent tags and detection antibodies. The incubation time is controlled by the second valve. When the desired incubation time is reached, the second valve is opened to allow the reaction mixture reach the fluid ejector array. The fluid ejector array ejects the reaction mixture onto the capture zone located beneath the ejector array. The rate of ejection of reaction mixture is controlled actively so that the reaction mixture has sufficient time to bind with capturing antibodies that are immobilized on the capture zone.

When the reaction mixture is completed ejected onto the capture zone or a desired amount, as is determined by the time the fluid ejector array is actuated, is reached the capture zone, the second valve is closed. At the same time, the third valve is opened to allow the buffer fluid flowing from buffer chamber to fluid ejector array. The rate of buffer fluid ejection is high enough such that the unbounded fluorescent tags on the capture zone are washed away by the buffer fluid into the waste chamber. The capture zone is then shined with a laser light to illuminate the captured conjugate of fluorescent tag and sample analyte. The level of fluorescent signal is thus proportional to the number of captured analytes.

BRIEF DESCRIPTION OF THE DRAWINGS

The foregoing and other objects of the invention will be more clearly understood from the following description when read in conjunction with the accompanying drawings of which:

FIG. 1 is a layout view of a micromachined microfluidics diagnostic device according to the preferred embodiment of the present invention.

FIG. 2 shows a cross-sectional view of a micromachined microfluidics diagnostic device according to the preferred embodiment of the present invention.

FIG. 3 shows a cross-sectional view of a reaction chamber for a micromachined microfluidics diagnostic device according to the preferred embodiment of the present invention.

FIG. 4 shows a top plan view of a first valve for a micromachined micromachined microfluidics diagnostic device according to the preferred embodiment of the present invention.

FIG. 5 shows a top plan view of a first valve for a micromachined microfluidics diagnostic device according to another preferred embodiment of the present invention.

FIG. 6 shows a top plan view of a second valve for a micromachined microfluidics diagnostic device according to the preferred embodiment of the present invention.

FIG. 7 shows a cross-sectional view of a reaction chamber for a micromachined microfluidics diagnostic device according to the preferred embodiment of the present invention.

FIG. 8 shows a cross-sectional view of a fluid ejector array for a micromachined microfluidics diagnostic device according to the preferred embodiment of the present invention.

FIG. 9 shows a top plan view of a fluid ejector array for a micromachined microfluidics diagnostic device according to the preferred embodiment of the present invention.

FIG. 10 shows a top plan view of a capture zone for a micromachined microfluidics diagnostic device according to the preferred embodiment of the present invention.

FIG. 11 shows a cross sectional view of a capture zone for a micromachined microfluidics diagnostic device according to the preferred embodiment of the present invention.

DESCRIPTION OF THE PREFERRED EMBODIMENTS

Temperature, incubation time, reagent and analyte concentration, kinetics, and washing quality are five key parameters affecting the performance of immunoassays. For micro- and nanoscale immunoassay systems, as the size decreases, so does the volume. At very small scales, surface tension becomes the dominant force while inertia is insignificant. As a result, the surface tension effects of the materials that come into contact with sample and reagents become very important. In aqueous biological fluids such as blood, urine, and sputum, additional intermolecular attractive forces create higher surface tension and increase viscosity. The variation of surface tension force with different sample fluid and/or reagent presents a significant challenge to the fluid/reaction mixture movement in the micro- and nano-scale immunoassays system.

The electroosmosis also presents another challenge to the micro- and nano-scale immunoassays systems. Samples and reagents contain ions that will interact with a charged surface. In order to move them, voltage may be applied to move them along a capillary.

The concentration of analyte in a sample is constant, regardless of the sample size. As the sample size is reduced, the number of molecules in the sample decreases. Another complication with very low sample volumes containing low concentrations of analyte concerns the effect of removal of analyte molecules from the solution as the assay incubation progresses. Immunoassays rely on the antibodies sampling the analyte. As the incubation progresses, it is preferable that the analytes are not depleted in the solution by antibody binding. Also as analyte concentration in the solution decreases, the amount of analyte dissociating from the antibody molecules increases.

Traditional microdevices based on microfluidics such as those reported in U.S. Pat. No. 6,905,882 and U.S. Pub. No. 2004/0171092 rely completely on the use of capillary forces to move the sample and reagent fluid around inside these microdevices. In order to achieve the capillary forces large enough to drive the sample and reagent fluids, the microchannels will have to be made on the order of capillarity scale. This, however, reduces the effect of advantage that is introduced by the miniaturization of immunoassays devices. The use of a reduced scale such as the microdevices has a significant advantage because it reduces the distances that molecules need to travel. But those traditional immunoassays devices have to compromise this advantage in order to move the fluid in the microdevices.

The active microdevice reported in U.S. Pat. No. 6,887,362 relies on the electric field (or electroosmosis) to move and analyze the analytes. Electroosmosis is most effective for nanoliter samples in a microdevice. But the low concentration of sample analytes will amplify the problem with this method of moving the fluid around in the microdevice, thereby compromising the immunoassays performance.

We approach the design of microdevice for immunoassays in different perspectives. We combine the advantages of a microdevice and the active control mechanism. According to the preferred embodiment of present invention, the micromachined microfluidics diagnostic device is comprised of a sample port, a first valve, a reaction chamber, a second valve, a fluid ejector array, a third valve, a buffer chamber, a capture zone and a waste chamber. The diagnostic device has layered structure, with the first layer being made of plastics, PDMS, SU-8 or other elastic materials. The formation of first layer can be accomplished by hot embossing, plastic molding, and pressing. The second layer of the diagnostic device is a semiconductor die that is micromachined on a silicon substrate, a glass substrate, a quartz substrate, or other substrates. The third layer of the diagnostic device can be the same material as the first layer, or another type of plastic material. These three layers of diagnostic device are aligned, bonded and sealed using glues, ultrasonic welding, or metallic binding.

Each of the components in the diagnostic device made according to preferred embodiment of present invention is interconnected with one another through microfluidic channels. The flow of sample and/or reaction mixture from one chamber to another is accomplished through the capillary force, electroosmosis effect, external driving force, or a combination of them. Active valves are timed by software to precisely control the amount of fluid flowing through the micro-channel into or out of the reaction chamber. The mixing of sample analytes, the fluorescent tags, and the detection antibodies are aided by the active mixer embedded at the bottom of the reaction chamber. The open and close of valves at both ends of the reaction chamber allows reaction mixture flow into the fluid ejector array for dispensing onto the capture zone. According to the preferred embodiment of present invention, the rate of ejection of reaction mixture is controlled such that the kinetics of binding the fluorescently tagged analytes and capturing antibodies is enhanced. The capturing antibodies are immobilized on the capture zone. When the liquid phase reaction mixture is ejected onto the capture zone, the analytes and capturing antibodies are kept close enough such that their separation is on the order of analytes diffusion length. This increases the reaction rate between the analytes and immobilized capturing antibodies, and decreases the time required for equilibrium to be reached. The assays can therefore be completed in a shorter time.

According to the preferred embodiment of present invention, the design of capture zone and fluid ejector array also helps to reduce the diameter of reaction vessel containing the immobilized antibodies over which the sample is flowing. This further reduces the assays time.

The effective removal of unbound signal generating fluorescent tags is crucial to the assay performance. The ultra-low concentration of bound label can only be measured precisely if all unbound label is washed away. According to the preferred embodiment of present invention, the washing of the unbound label is accomplished by the fluid ejector array ejecting the buffer fluid onto the capture zone. In the washing stage, the rate of fluid ejection is controlled in the software such that fluid pressure reaching capture zone surface is enough to move away the unbound fluorescent tags, but the bound conjugates are unharmed.

Referring now to FIG. 1, which shows the general layout of a micromachined microfluidics diagnostic device 1 according to the preferred embodiment of present invention. It is comprised of a sample port 2, a first valve 3, a reaction chamber 4, a second valve 5, a fluid ejector array 6, a third valve 7, a buffer chamber 8, a capture zone 25 and a waste chamber 9. All the components of the micromachined microfluidics diagnostic device are interconnected through micro channels 10. FIG. 2 shows the cross-sectional view of the diagnostic device 1. It has a layered structure, with each different layers bonded or welded to each other. The first layer 24 is made of plastics, PDMS, SU-8 or other elastic materials. The formation of first layer 24 can be accomplished by hot embossing, plastic molding, or pressing. In the first layer 24, there are molded with sample port 2, top part of reaction chamber 4, top part of fluid ejector 6, the buffer chamber 8 and interconnecting micro channels 10. The second layer 23 of the diagnostic device 1 is a semiconductor die that is micromachined on a silicon substrate, a glass substrate, a quartz substrate, or other substrates. Micromachined on the second layer 23 are active components the first valve 3, the active mixer at the bottom of reaction chamber 4, the second valve 5, the bottom part of fluid ejector array 6, and a third valve 7. The third layer 22 of the diagnostic device 1 can be the same material as the first layer 24 of the diagnostic device 1, or another type of plastic material. Molded into the third layer 24 are a cavity 27 which allows the seating of capture zone 25, the waste chamber 9 and micro channel 26 that connects the capture zone 25 and waste chamber 9.

The cross section of sample port 2 is illustrated in FIG. 3. The sample port 2 has an inlet 31 to allow the addition of raw blood or plasma to the upper chamber 32. There is a built-in filter 21 in the sample port 2 that divides the upper chamber 32 and lower chamber 33. The filter 21 is needed to separate blood plasma, which is the analyte sample for assaying, from white or red blood cells or other contaminants. To improve the filtering effect, a thin layer of polymer material 34 may be coated on top of the filter 21. On walls of lower chamber 33, an anti-coagulation coating 35 may be painted. The sample port 2 is connected to the first valve 3 through micro channel 10, which is located at or near the bottom of the lower chamber 33.

FIG. 4 shows the top plan view of the first valve 3 section of the diagnostic device 1 according to the preferred embodiment of present invention. The first valve 3 has active section 44 micromachined on the second layer 23 of the diagnostic device 1. Overlaid on top of the first valve 3 is the micro channel 10. The micro channel 10 has a narrower section 42 and wider section 41 interconnected. The combination of narrower section 42 and wider section 41 forms a capillary stop valve. Adjusting the dimensions of wider section 41 and/or narrower section 42, such as the channel height, width, and length, creates the capillary stop value at different levels. The contact angle 43 that joints the wider section 41 and narrower section 42 can also be adjusted to change the capillary stop value. The contact angle 43 can be adjusted to be less or greater than 90 degrees, as shown in FIG. 5.

The top plan view of the second valve 5 and third valve 7 section of the diagnostic device 1 is shown in FIG. 6. In this section of the micro channel 10, it has a wider cross section 44 and narrower cross section 45. The micro channel 10 is tapered from the wider cross section 44 to narrower cross section 45. Under capillary forces, the fluid will flow in this direction, passing the second valve 5 or third valve 7. When the second valve 5 or third valve 7 is actuated, the fluid flowing through this section of micro channel 10 is stopped.

FIG. 7 shows the cross sectional view of a reaction chamber 4. The reaction chamber 4 has a cavity 51, and an active mixer 52 at the bottom. The active mixer 52 is micromachined in the second layer 23 of the diagnostic device 1. On top of the active mixer 52, dry coated material 52 is placed which contains reagent, fluorescent tags and/or detection antibodies. When the plasma solution is entered into the reaction chamber 4 from the sample port 2 through micro channel 10, it mixes with the dry coated material [[52. After the cavity 51 of reaction chamber 4 is fully filled or a determined amount of plasma is entered into cavity 51, the active mixer 52 is actuated to aid the mixing of plasma with dry coated material 53. Analytes in the plasma then binds with fluorescent tags and detection antibodies in the dry coated materials 53.

The cross sectional view of a fluid ejector array 6 according to the preferred embodiment of present invention is illustrated in FIG. 8. The ejector array 8 comprises an elastic membrane 61 that has a scalable amount of orifices 60 on it and is supported by the substrate 23. On top of the membrane 61, there are piezoelectric transducers 62 that are evenly spaced on them. An isolation layer 63, which prevents the electrode of piezoelectric transducers 62 in direct contact with the fluid that is to be ejected, is coated on top of the piezoelectric transducers 62. The elastic membrane 61 may be conductive, in which case it acts as a common electrode for transducers 62. A reservoir 65, which is used to store the fluid to be ejected, is bounded by the elastic membrane 61, sidewall 67 and a top cover 64. At both ends of sidewall 67, fluid inlets 70 are cut from the sidewall 67 and connected with micro channel 10 to allow the fluid filling in the reservoir 65. Both sidewall 67 and top cover 64 may be made of plastics, PDMS, acrylics or other non-conductive materials, and bonded to the micromachined substrate base. The sidewall 67 and top cover 64 may also be micromachined by sacrificial etching. Cavity 69 is formed by etching away a part of bulk substrate 23 during the micromachining.

In another preferred embodiment according to present invention, the top cover 64 has a piezoelectric layer 66 bonded on top of it. This piezoelectric layer 66 will vibrate transflexurally to cause the top cover 64 buckle up and down, thereby ejecting fluid droplets 68 from the orifices 60. The piezoelectric layer 66 may be located at the bottom of the cover plate 64, according to a further preferred embodiment of present invention. In this case, the piezoelectric layer 66 can be molded into the first layer 24 of the diagnostic device 1.

FIG. 9 shows the top plan view of the micromachined fluid ejector array 6 according to preferred embodiment of present invention. Piezoelectric transducers 63 form concentric rings surrounding the center of fluid ejector array. These piezoelectric transducers 63 may have same width or different widths. Between neighboring piezoelectric transducers 63, there are a scalable array of orifices 60 drilled on the elastic membrane 61. The diameter of the orifices 60 may be same or different, depending on the particular applications. Orifices 60 are arranged uniformly at the center of neighboring piezoelectric transducers 63.

In one mode of operation, the neighboring piezoelectric transducers 63 are applied with electric voltage to cause the elastic membrane 61 to deflect up and down. The orifices 60 that are arranged between them will vibrate to eject fluid droplets 68. If all piezoelectric transducers 63 are actuated, all orifices 60 will eject fluid droplets 68 at the same frequency that the piezoelectric transducers 63 are driven.

In another mode of operation, the bulk actuation waves have an amplitude large enough to eject fluid droplets through orifices 60 in phase. The bulk actuation wave is generated by applying electric signals on piezoelectric layer 66. The alternating electric signal will cause the top cover 64 to buckle up and down. The buckling of top cover 64 generates the bulk pressure wave in fluid inside the reservoir 65. If this bulk pressure is large enough such that it overcomes the capillary forces that keep fluid in the orifices 60, the droplets 68 will be ejected from orifices 60.

FIG. 10 shows the top plan view of a capture zone 25 made according to the preferred embodiment of present invention. The capture zone 25 has concentric ridges 71 arranged on the capture zone 25 surfaces. These ridges 71 are spaced uniformly or non-uniformly across the entire surface area of capture zone 25. There are openings 72 between sections of ridges 71. On the capture zone 25, there are also a plurality of capture cells 73 scattered on its surface. These cells 73 contain immobilized capturing antibodies for assays. As the reaction mixture or buffer fluid is ejected down from the fluid ejector array 6, the fluid flows over these capture cells 73. The fluorescent tagged analytes bind with capturing antibodies, and become immobilized conjugates.

In another preferred embodiment of present invention, the capturing cells 73 can simply be a thin layer of coating on the capture zone 25 surface. As the reaction mixture is ejected from the fluid ejector array 6 to capture zone 25, the fluid flows on this thin layer of coating. The analytes thus bind with capturing antibodies. The waste fluid thus flows further into the waste collection channel 74. Through a micro channel 75, these waste is collected in the waste chamber 9.

FIG. 11 shows the cross section of capture zone 25 along line AA' of FIG. 10. The capture zone 25 has a domed surface 76. Concentric ridges 71 are arranged on this surface 76. According to one preferred embodiment of present invention, these ridges 71 have the effect of slowing the fluid that flows over the domed surface 76 of capture zone 25, thus increases the rate of binding analytes with immobilized antibodies coated on the surface 76. In another preferred embodiment of present invention, the domed surface 76 helps focus the fluorescent signals emitted by the fluorescent tags bound on its surface, and generates strong enough signal level to be detected.

According to one preferred embodiment of present invention, the height of concentric ridges 71 is high enough to slow down the flow of reaction mixture, but low enough not to present obstacles to the flow of buffer fluid for washing away unbound fluorescent tags. When buffer fluid is ejected from the fluid ejector array 6 onto the domed surface 76 of capture zone 25, it washes away unbound fluorescent tags on the domed surface 76. The waste flows into the waste collection channel 74, and further flows into waste chamber 9.

As illustrated in FIG. 11, the bottom of capture zone 25 is flat, and has a thin layer of third layer 22 of the diagnostic device 1. The body of capture zone 25 and this third layer 22 is transparent, to allow the passage of laser light to shine the bound fluorescent tags captured on the domed surface 76 of capture zone 25.

For those skilled in the art, the diagnostic device 1 according to one preferred embodiment of present invention is considered as one channel for immunoassays. And hence according to another preferred embodiment of present invention, the micromachined microfluidics diagnostic device 1 has multiple channels, each of these channels is used for assaying one particular analyte. Each channel has its own sample port 2, or share a common sample port 2. But each channel has its own reaction chamber 4, a first valve 3, a second valve 5, a third valve 7, and a fluid ejector array 6. All these channels may share a common buffer chamber 8 and waste chamber 9 or has its own buffer chamber 8 and waste chamber 9.

The foregoing descriptions of specific embodiments of the present invention are presented for the purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A method of analyte analysis, the method comprising:
providing a diagnostic device comprising: a sample port in fluid contact with a reaction chamber through a first channel, a fluid ejector array in fluid contact with the reaction chamber through a second channel and comprising one or more orifices positioned over a cavity, and a capture surface in the cavity below the orifices;
introducing analytes in a fluid to the sample port to flow through the first channel and to contact a reagent in the reaction chamber, wherein the analyte binds or reacts with the reagent;
flowing the bound reagent or reacted reagent through the second channel to the fluid ejector array;
ejecting the bound reagent or reacted reagent in droplets from the array orifices through the cavity on to the capture surface; and,
detecting bound or reacted reagent on the capture surface.

2. The method of claim 1, wherein reagent comprises a detection antibody and the capture surface comprises one or more capture antibodies.

3. The method of claim 1, further comprising controlling a flow in the channels by: controlling active valves on the channels, controlling ejections from the orifices, or providing a contact angle in a channel.

4. The method of claim 1, further comprising regulating an electronically controllable valve in one or more of the channels to control a reaction time of the analyte and reagent in the reaction chamber.

5. The method of claim 1, further comprising washing the capture surface by ejecting a wash buffer from the array orifices onto the capture surface.

6. The method of claim 1, wherein said ejecting comprises actuation of a piezoelectric transducer.

7. The method of claim 1, wherein said detecting comprises shining a laser light through the capture surface to illuminate the bound reagent or reacted reagent.

8. The method of claim 1, further comprising providing two or more of the diagnostic devices on a chip.

9. The method of claim 1, wherein said providing the diagnostic device comprises sandwiching a micromachined layer comprising the ejector array between two plastic layers to form a layered structure.

\* \* \* \* \*